United States Patent
White (10) Patent No.: US 6,935,859 B2
(45) Date of Patent: Aug. 30, 2005

(54) METHOD FOR FABRICATING ORTHODONTIC APPLIANCES

(76) Inventor: Velton C. White, 590 Kearney Rd., Burlington, WI (US) 53105

( * ) Notice: Subject to any disclaimer, the term of this patent is extended or adjusted under 35 U.S.C. 154(b) by 319 days.

(21) Appl. No.: 10/419,607

(22) Filed: Apr. 21, 2003

(65) Prior Publication Data
US 2003/0198915 A1 Oct. 23, 2003

Related U.S. Application Data (60) Provisional application No. 60/374,554, filed on Apr. 22, 2002.

(51) Int. Cl.[7] .................................................. A61C 3/00
(52) U.S. Cl. .............................. 433/24; 433/6; 433/21
(58) Field of Search ............................. 433/24, 18, 21, 433/213, 6

(56) References Cited

U.S. PATENT DOCUMENTS

| 5,580,243 A | * | 12/1996 | Bloore | 433/6 |
| 2003/0013062 A1 | * | 1/2003 | White | 433/21 |

* cited by examiner

Primary Examiner—Cary E. O'Connor
(74) Attorney, Agent, or Firm—Dorr, Carson, Sloan, Birney & Kramer, P.C.

(57) ABSTRACT

A method for fabricating a removable orthodontic appliance with lingual springs using a model of a patient's teeth. One or more ideal reference grooves (e.g., a central ideal reference groove, occlusal ideal reference groove, or gingival ideal reference groove) are cut into the lingual surfaces of the model teeth reflecting the desired, ideal positions of these teeth after orthodontic treatment. The orthodontic appliance is then cast on the model with the stem of each lingual spring stem embedded in the appliance and the tooth-contacting end of each lingual spring positioned in the reference groove of a model tooth.

15 Claims, 5 Drawing Sheets

METHOD FOR FABRICATING ORTHODONTIC APPLIANCES

RELATED APPLICATION

The present application is based on, and claims priority to the Applicant's U.S. Provisional Patent Application No. 60/374,554, entitled "Method For Fabricating Orthodontic Appliances," filed on Apr. 22, 2002.

BACKGROUND OF THE INVENTION

1. Field of the Invention

The present invention relates generally to the field of orthodontic appliances. More specifically, the present invention discloses a method for fabricating orthodontic appliances that include lingual springs.

2. Statement of the Problem

In dentistry, and more particularly in orthodontics, a central step typically accomplished at the beginning of many types of treatment is the taking of impressions of a patient's teeth. From such negative impressions, positive stone models of a patients upper and lower teeth, gums and palate can be reproduced and in this way, stone models duplicate virtually all aspects of a patient's oral anatomy. The availability of such stone models, called study models, provides the attending orthodontist with full information needed to diagnose an individual's malocclusion and devise an indicated treatment plan. From the study models, the full extent and nature of a malocclusion can be quantified and a viable treatment sequence for correcting a malocclusion can be established, which is known as a patient's treatment plan.

After taking a patient's impressions, an orthodontist may ask his staff to pour multiple, duplicate sets of a patient's models, particularly if it is likely that a patient's treatment plan may require appliances that are to be fabricated by an outside orthodontic support laboratory. These are termed "working models". With multiple sets of models available at the beginning of orthodontic treatment then, the study models can remain available for the orthodontist to use for establishing the patient's treatment plan and the working models may be sent to an orthodontic laboratory along with the doctor's prescription for fabricating a specific appliance for the patient.

Stone models have many inherent attributes that facilitate fabrication of laboratory-produced appliances. For example, laboratory technicians may first grind inter-proximal material from a stone model to fully expose the crowns of the "stone" first molars. With the upper and lower first molars exposed in this manner, laboratory technicians can select and confirm the exact size from a series of molar band or crown sizes that best fit the patient's molar teeth. Those bands or crowns once identified are typically left in a tight fitting, fully seated position on the molars of the working model.

Since the stone models are poured from fine dental stone, once cured they exhibit the properties of a refractory material. High temperature brazing and soldering operations can be performed directly on or in a working model without smoke, distortion or deterioration of the accuracy of the model. A typical laboratory operation would first include the selection and seating of bands or crowns on the molars as described above. Then, a laboratory technician would skillfully size, adapt and contour various hard stainless steel wires in accordance with features of the model. Such wires would be appropriately positioned adjacent to the seated bands. Once the wires are contoured and positioned in this manner, a lab technician can then use a biocompatible silver-based brazing alloy to braze the wires and bands together as a single assembly. In this way, the superstructure of one type of current laboratory-produced orthodontic appliances is fabricated.

In another common and well-known laboratory process used for fabricating appliances, the surfaces of a model are first coated with a release agent. After receiving such a release coating, dental acrylic (e.g., poly methyl-methacrylate monomer and powder) or other commercially available rigid castable plastic dental materials can be cast directly on or within a stone model. Once such a polymeric mass is cured and removed from the model, it retains all of the subtle contour features and overall shape and size of the palate and the teeth present in the model. In this manner, the familiar orthodontic retainer and many other types of functional or orthopedic orthodontic appliances that consist at least in part of plastic components are formed. Further, various auxiliary appliance components such as expansion screws, springs, hooks, and hinges and other metallic orthodontic appliance components can be potted into the dental acrylic as part of the construction of a typical orthodontic appliance. To pot or embed metallic components into the polymeric superstructure of such an appliance, the components are first positioned within the patient's stone model in a manner specified in the attending doctor's prescription. Once positioned, they are temporarily held in place by a structural wax material commonly used in dental laboratories. Then, the laboratory technician will apply a slurry of uncured dental acrylic that surrounds and partially flows over the components as positioned. Once the dental acrylic cures, the various metallic components will be embedded in place within the dental acrylic.

Typically, the fabrication of an orthodontic appliance by an orthodontic laboratory will first involve seating of bands or crowns that fit upon the anatomy of various teeth in the stone model. Then various stainless steel wires will be adapted and brazed in place. This will then be followed by the casting of dental acrylic. Such acrylic appliances may be of a monolithic configuration, or they may be divided into halves, or into right and left halves with a third front section, where all of these sections are intended to move relative to each other in certain expansive ways. Most appliances will include metallic components in combination with dental acrylic but other appliances may be formed from metallic components only, and yet others are formed entirely of dental acrylic. As a rule, metal-only appliances are considered to be "fixed" in that they are permanently affixed to teeth in the mouth and are removable only by the orthodontist. Appliances that are predominantly acrylic are usually classified as "removable" in that such appliances can be removed and reinserted at any time by the patient.

As described, all of the fabrication steps described are accomplished using the patient's working models as a fabrication pattern or fabrication template. The underlying reason for this, and the advantage of using the stone models in this manner, is that once the appliance is completed by the laboratory and shipped to the attending orthodontist, the appliance can be installed directly in the patient's mouth and upon initial insertion, it will exhibit a desired accurate and intimate fit relationship with the teeth, gums and palate of the patient. The fit achieved through this process applies equally to both fixed and removable type appliances.

The ideal fit achieved by an appliance fabricated using this process was first described above as occurring at the beginning of treatment. However, in other cases, the use of this type of appliance may not be indicated until a later phase of treatment. In all cases, fresh impressions must be taken at the time of fabricating such an appliance to produce stone models that reflect the patient's oral realities and treatment progress at that time. Otherwise the finished appliance will not intimately fit in the patient's mouth as required.

Using laboratory-fabricated appliances for orthodontic correction requires that such appliances embody devices that actively generate corrective forces and at the same time, other devices and features that are intended to remain passive and stationary. Normally, such passive features are the larger superficial features of the appliance that serve to provide stability and retention of the appliance within the mouth through direct contact with the gums, palate and some of the teeth. Such passive features thereby serve as a base, anchor, or foundation for the active features of the appliance.

The active features of an orthodontic appliance are those that are capable of generating and imparting desirable corrective orthodontic forces to the teeth in the orthodontic sense, or corrective forces to the malleable bony structures surrounding the oral cavity in an orthopedic sense. It is possible to categorize such active forces that are typically generated by laboratory-produced appliances into two groups. First are those forces that are generated by periodic activation of sub-components of the appliance (e.g., expansion screws). A second category of active forces are those forces that are generated by the loading of various types of springs that store energy.

The latter category of active devices typically employed in laboratory-produced orthodontic appliances that store energy includes various types of springs, which are skillfully positioned within the stone model during fabrication of the appliance. Important to the appreciation of the present inventive methodology, such springs must be positioned anticipatorily. In other words, the laboratory technician must place them within the model in a way that would hypothetically render them passive only at a hypothetical future point in time where the teeth have all been moved to their ideal positions. In yet other words, a laboratory technician must anticipate the ideal corrected positions of each maloccluded tooth, and position any springs associated with that tooth in a positional relationship to that tooth so that after the spring has unloaded its stored energy over time, it has moved the tooth into its corrected position. And in doing so, the spring then becomes passive to that ideally-positioned tooth and will move it no further. To a large extent, the ability of a laboratory technician to achieve this complex and anticipatory task determines his or her level of skill.

Carrying the concept of anticipatorily positioning of springs further, it can be appreciated that upon first placing such a configured appliance in a patient's mouth, each anticipatorily-positioned spring will be deflected by the tooth it is intended to move and thereby loaded according to the degree to which the pre-treatment position of that tooth varies from its ideal position. As can be seen then, it is the action of the mal-positioned teeth acting against, and deflecting the springs that loads the springs, and it is the resulting stored energy from such loading that is slowly dissipated over time as the teeth positionally respond, and over time move in desired directions.

Based on the described need for a laboratory technician to accurately anticipate the teeth in their final and finished aesthetic positions while fabricating an orthodontic appliance, it has become a well known practice for the laboratory technician to undertake a time-consuming and laborious process called "resetting the model." A reset model is identical to an original model except that it will exhibit most or all of the stone teeth in an ideal position or occlusion, having been cut free of the model and from each other, and then skillfully and individually repositioned into ideal occlusion.

Resetting a stone model in this manner requires the use of special thin saws to cut between each tooth to a point well below the gingival margins of the teeth. In practice, two divergent cuts are actually made between each tooth and its adjacent tooth. The divergent configuration of the two cuts between adjacent teeth creates a tapered wedge of standing stone material that can be broken out free of the model. After that, the individual teeth themselves can be similarly snapped free from the model. The laboratory technician will then reposition the teeth on the model using a heated wax material known as "base plate wax" that hardens at room temperature.

The wedge of stone material described above as being removed from between adjacent teeth creates open space associated with the roots of the teeth that permits the freedom for a tooth to be uprighted in angulation if required. In rotation, the stone teeth can be individually manipulated and positioned by the laboratory technician and aligned by the use of thumb and forefinger pressure applied to a group of teeth and similarly, a single tooth or a group of teeth can be adjusted in torque by finger manipulation.

The wax material bonds the repositioned teeth securely to the model, but the entire model can be heated to soften the wax. Once softened, subtle adjustments can be made to a single tooth or groups of teeth, allowing the technician to ensure that he or she has placed the stone teeth in a close approximation of an ideal occlusion to the degree that such a resetting process permits.

During the process of fabricating an orthodontic appliance and specifically after the step of resetting the model, the dental acrylic components of an appliance can be flowed into and cast within the model. During this process, but prior to actually applying the uncured slurry of acrylic powder and monomer, the laboratory technician can place springs passively in contact with the "corrected" stone teeth. Such spring devices are similarly held in their desired positions by the wax material. It is important to note that once the dental acrylic is applied and cured, the springs will then be held rigidly in their pre-determined positions, with their active end resting passively against the corrected stone teeth, and with stem embedded rigidly in the polymeric substrate.

The incorporation of the resetting step during the fabrication process greatly reduces the challenge and complexity of the task faced by the laboratory technician where he or she must anticipate and imagine the ideal final positions of the teeth. By resetting the teeth into their final, treated positions, all of the guessing is eliminated. Considering all of this then, one can see that it is the true positional discrepancy between the ideally placed stone teeth and the patient's actual mal-occluded teeth that will deflect and thereby load the springs as an appliance fabricated in this manner is initially placed in the mouth and pushed into a fully-seated position at an initial trial fitting.

Even though the step of resetting a patient's stone models is undertaken to reduce the anticipated challenge and complexity of fabricating a quality appliance, and to more closely approximate the finished results of treatment, the resetting process itself introduces a number of problematic shortcomings. First, subtle variances or excesses of inward or outward canting of the reset teeth in torque can drive a significant cumulative error in total arch length. In other words, the sum of effective tooth widths around an arch can vary significantly depending on any subtle lingual or labial inclinations of the teeth. The difference between total arch length of an appliance built from a reset stone model and the patient's actual arches can typically amount to 2 mm or more. In such a case, an appliance may fit poorly in the patient's mouth and may be capable of generating excessive binding forces to the teeth. Such excessive forces can injure the supporting structures of the teeth as well as cause patient discomfort. Another shortcoming of the resetting process is that after the teeth have been repositioned, the relationship between the reset crowns of the teeth and the underlying supportive bone may have been disrupted. For example, if the repositioned crown predicts that the root of the tooth will be located outside of what is known as the alveolar trough, the resulting appliance will be predisposed to move the teeth and their roots into an area of bone that cannot mechanically support the root, or worse, an area of bone where the root cannot be orthopedically moved too. An appliance that is predisposed to attempt to achieve these impossibilities is destined to cause major problems for both the orthodontist and patient alike.

There is also another problem associated with resetting the teeth involving those teeth that may already be in desirable positions and therefore do not require movement. Portions of an acrylic appliance may be cast so that the acrylic is intentionally encouraged to flow up and onto a portion of the dental crown of a tooth. When cured, that portion of the acrylic in intimate contact with the tooth can serve to stabilize and hold the tooth in precise position. Through the resetting process, however, that precise intimate fit relationship between the acrylic and the tooth is lost. The employment of such an accurate fit between some of the teeth and the acrylic portion of an appliance cannot be achieved with an appliance fabricated from a reset model because the necessary positional accuracy is lost during the resetting process.

As can be appreciated from all of the foregoing, the step of resetting a stone model is undertaken in an attempt to increase the accuracy and effectiveness of the appliance that emerges from the stone model and to reduce the complexity and challenge in imagining the finished positions of the teeth. Resetting requires specialized skills on the part of the laboratory technician and a significant amount of time. It involves a great deal of cutting of the stone model and an associated mess, and as described above, the reset model has shortcomings resulting from the resetting process itself. All of these factors combine to increase the cost, complexity and administrative logistics faced by an orthodontist in delivering orthodontic treatment.

3. Solution to the Problem

In contrast to prior art methodologies, the present invention uses a number of ideal reference grooves cut into the lingual surfaces of the model teeth to position lingual springs in an orthodontic appliance. The present methodology serves to achieve all of the advantages of the resetting process while avoiding the various problems, cost and shortcomings associated with the resetting process.

SUMMARY OF THE INVENTION

This invention provides a method for fabricating an orthodontic appliance that includes lingual springs. First, a model of the patient's teeth is cast in the conventional manner. One or more ideal reference grooves (e.g., a central ideal reference groove, occlusal ideal reference groove, or gingival ideal reference groove) are then cut into the lingual surfaces of the model teeth. The location of the floor of such a groove reflects the desired, ideal positions for these teeth after treatment. The orthodontic appliance is cast on the model using the ideal reference grooves on the tooth to position the tooth-contacting portion of each lingual spring.

These and other advantages, features, and objects of the present invention will be more readily understood in view of the following detailed description and the drawings.

BRIEF DESCRIPTION OF THE DRAWINGS

The present invention can be more readily understood in conjunction with the accompanying drawings, in which.

DETAILED DESCRIPTION OF THE INVENTION

As a preliminary step in the present invention, a model of the patient's teeth is cast in the conventional manner, as previously discussed. For example, a rear perspective view is provided in FIG. 1 of a lower stone model 10 of a patient's occlusion. One of the lower incisors 1R is undesirably lingually disposed and another lower incisor tooth 2R exhibits an undesirable distal-lingual rotation.

A number of ideal reference grooves are then cut into the lingual surfaces of the model teeth reflecting the desired, ideal positions for the lingual-most extent of the lingual surface of the crown of these teeth after treatment. In the case of tooth 1L in FIG. 1, an imaginary horizontal arc that defines an ideal lingual radius of all of the lower anterior teeth passes through tooth 1L in a tangentially grazing fashion because tooth 1L is already in an ideal labio-lingual position and exhibits no undesirable rotation. In contrast, the imaginary ideal lingual radius arc passes more deeply through tooth 1R due to its undesirable lingually disposed position. Tooth 2R exhibits the ideal lingual radius arc passing more deeply through its distal-lingually rooted portion.

Figure 1:
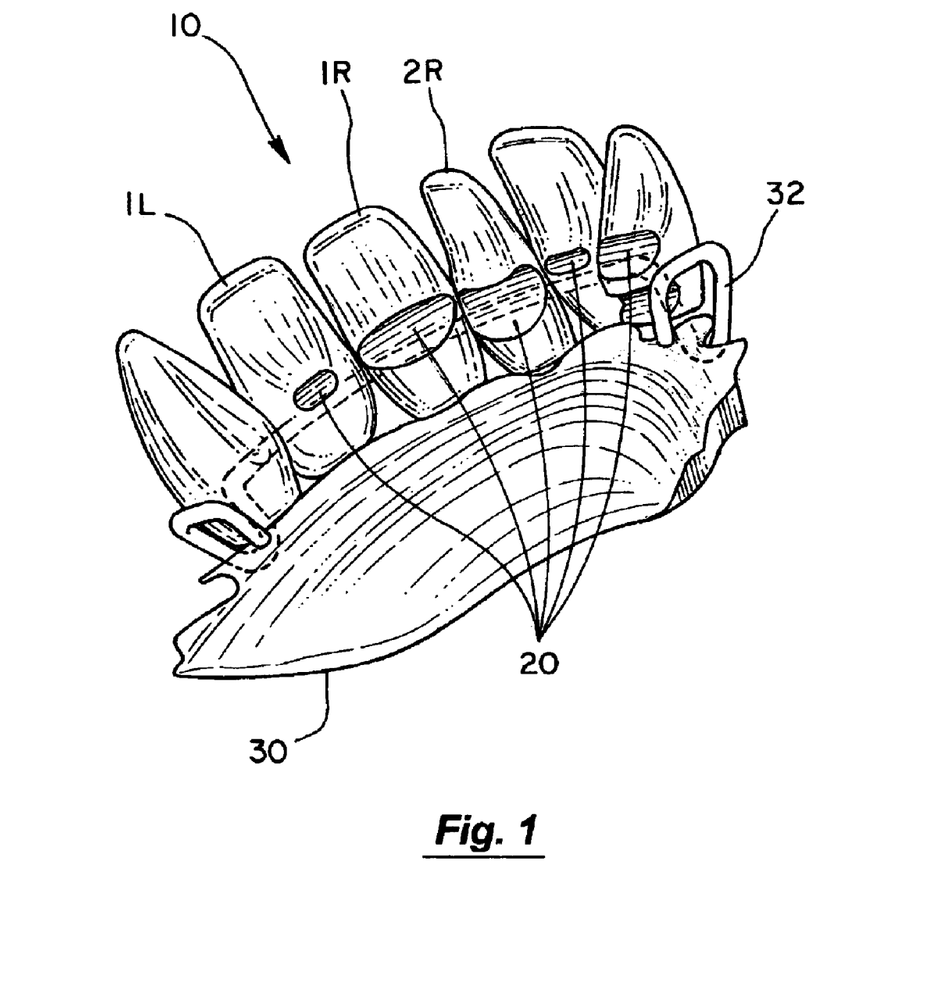
FIG. 1 is a rear perspective view of a model 10 of a patient's lower anterior teeth also showing a portion of an orthodontic appliance 30 with a labial bow 32. A central ideal reference groove 20 (CIRG) has been cut into the lingual surfaces of the teeth in the model 10.

FIG. 1 also shows an orthodontic appliance 30 in position on the stone model 10. The teeth shown in FIG. 1 should be understood as representing "stone" teeth and it should be understood that such an appliance 30 as shown would be in the process of construction within the stone model 10 as it would be fabricated within an orthodontic laboratory.

Figure 6:
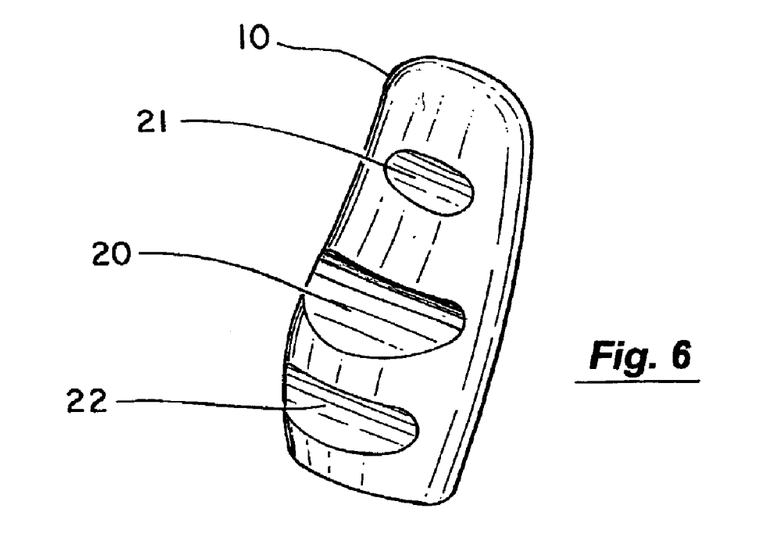
FIG. 6 is a rear perspective view of a model tooth 10 having a central ideal reference groove 20, an occlusal ideal reference groove 21, and a gingival ideal reference groove 22.

The lingual surfaces of most of the teeth have been relieved with a central ideal reference groove 20 (CIRG). It is referred to as "central" because it falls in the central third of the lingual surface of the teeth, roughly equidistant from the occlusal edge and the gingival margin. The lower right cuspid, (the right-most tooth shown in FIG. 1) can be seen with a gingival ideal reference groove feature 22 (GIRG). It should be understood that other teeth might have an occlusal ideal reference groove 21 (or OIRG), as illustrated in FIG. 6, although no occlusal ideal reference grooves are shown in FIG. 1. In the preferred embodiment of the present invention, an ideal reference groove is a groove that a laboratory technician will grind into the lingual surfaces of the stone teeth 10 using abrasive disks or edge cutting wheel mounted in hi-speed, hand-held hand pieces.

Central to understanding the present inventive methodology, it must be appreciated that the ideal reference grooves 20–22 are to be abrasively ground into the lingual surfaces of the stone teeth 10 in a manner that would place the labial-most extent of such a groove, at a labio-lingual point that anticipatorily coincides with the lingual most location of that tooth at the end of treatment when all of the teeth have been corrected to ideal positions. The arcuate trajectory of such a groove is to be considered as coincident with an imaginary ideal arc where such an imaginary ideal arc would tangentially graze each tooth once it has been ideally positioned at the end of treatment. Such imaginary arcs (e.g., the OIRG, CIRG and GIRG grooves shown in the figures) are ground following the ideal arc. To better define them, they should ideally meet the following criteria:

a) The center point of the radius of such an imaginary arc is centered on the saggital midline of the stone model, or stated differently. The radius of such an imaginary arc is to be centered and symmetrical with the patient's arch.
b) The center point of the imaginary arc is held constant and immovable as the imaginary arc, and the associated groove is ground through the various teeth.
c) The radius of the imaginary arc is constant as the imaginary arc is struck.
d) The actual radius value and center point location of the imaginary arc matches the ideal lingual radius established for an individual patient and falls on the saggital centerline of an individual patient's dental arch.

In the foregoing, the present inventive methodology is described as being applicable for considerations of the anterior teeth. It should be understood that other imaginary ideal arcs defining the ideal lingual extent of the teeth of the buccal and posterior segments can extend distally from either side of the ideal anterior arc and that such distally-extending arcs will be trigonometrically tangent to the central anterior arc but will exhibit a larger radius value than the anterior radius.

So, to fully appreciate the nature of a system of ideal imaginary arcs, regardless of whether they are located occlusally, centrally or gingivally, or oriented relative to the anterior, buccal or posterior segments, it must be understood that a series of tangential ideal arcs would minimally contact or graze each of the ideally-positioned teeth tangentially, and would not pass substantially through any of the teeth provided the teeth are ideally positioned, and therefore, the extent that such an imaginary arc does violate any one tooth of a stone model is directly proportional to the degree and extent that each tooth is orthodontically mal-positioned.

Figure 2:
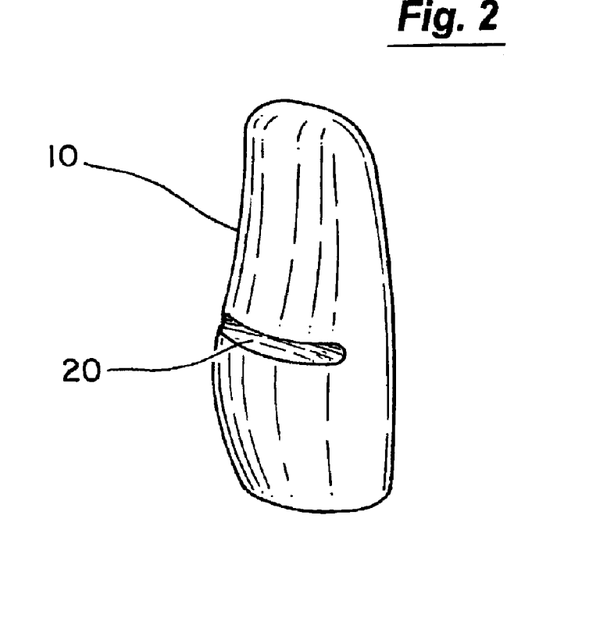
FIG. 2 is a rear perspective view of a single tooth in the model 10 with a CIRG 20.
Figure 3:
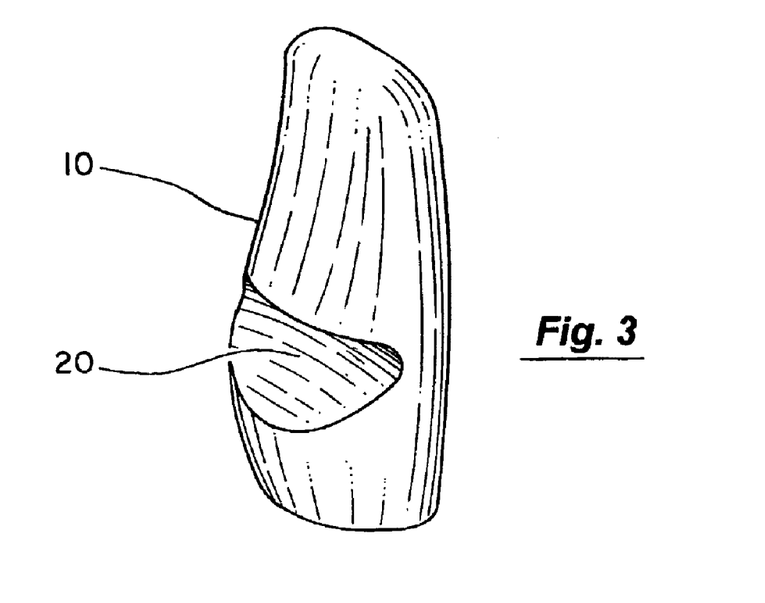
FIG. 3 is a rear perspective view of a model tooth 10 with an enlarged CIRG 20.
Figure 9:
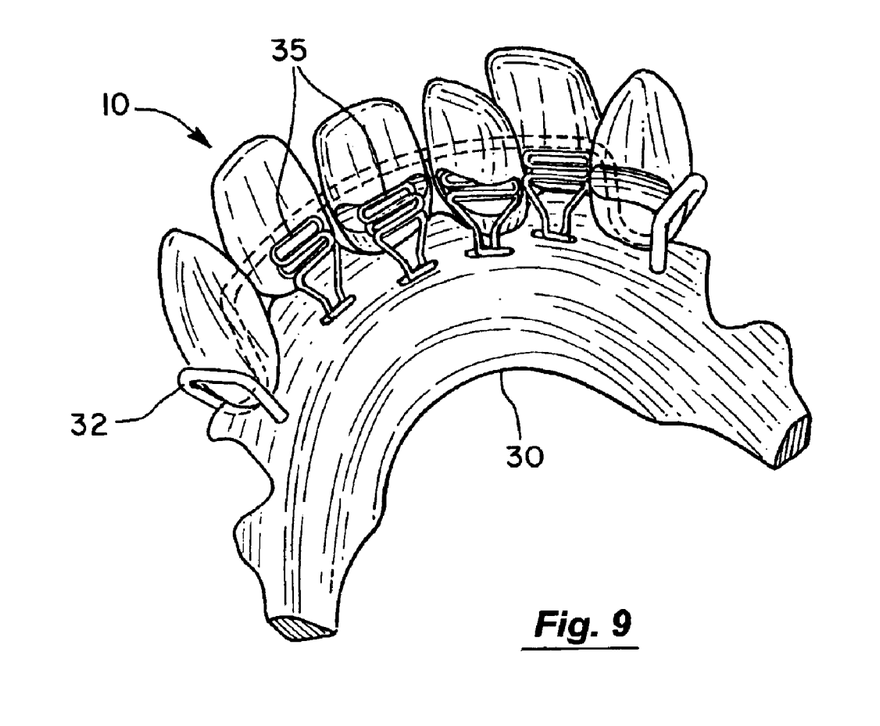
FIG. 9 is a rear perspective view of a model 10 of a patient's lower anterior teeth corresponding to FIG. 1, also showing a portion of an orthodontic appliance 30 with a labial bow 32 and lingual springs 35.

Conceptually, such an ideal CIRG arc, as it passes through any one mal-positioned tooth could be considered as looking like the example shown in FIG. 2, in which the depth and trajectory of such a groove indicate the full nature of the mal-position of the tooth. In practice, the groove ground by a lab technician into a tooth will be configured as shown in FIG. 3. As can be seen in FIG. 3, additional stone material may be removed from the tooth, even though the labial-most extent of the groove, or the "floor" of the groove remains coincident with the conceptualized floor shown in FIG. 2. The additional material is removed to accommodate any one of a group of lingually-mountable springs that are a part of an orthodontic appliance. Such springs are positioned and embedding in the acrylic mass of such an appliance and there is a registration relationship between the spring and the floor of an ideal reference groove ground into the model teeth. Two such springs are shown in registration with a CIRG 20 and a GIRG 22, respectively, in FIGS. 4 and 5. FIG. 9 illustrates a completed appliance 30 with several lingual springs 35. The base of each lingual spring 35 is stationary, being embedded in the cast-mass appliance 30, while the tooth-contacting portion of each spring 35 is positioned to rest in the floor of one of the ideal reference grooves 20–22.

To fully appreciate the advantages and benefits of the present inventive methodology, and to better describe the specific configuration of the types of lingual springs typically employed in the processes described above, U.S. Pat. No. 4,026,023 (Fisher) discloses a closed flap-type lingual spring. The present inventor's U.S. patent application Ser. No. 10/011,574, entitled "Orthodontic Appliance," also discloses an improved spring particularly suitable for use with the present inventive methodology. The present inventive methodology can be accomplished using other types of springs and devices that are well known in the field of orthodontics and such use will be readily apparent to one skilled in orthodontics and orthodontic laboratory practice.

Figure 4:
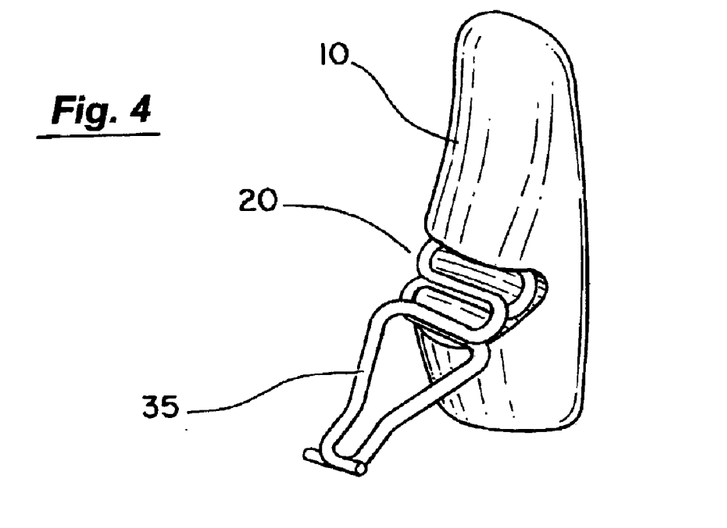
FIG. 4 is a rear perspective view of a model tooth 10 showing placement of a lingual spring 35 in the CIRG 20.
Figure 5:
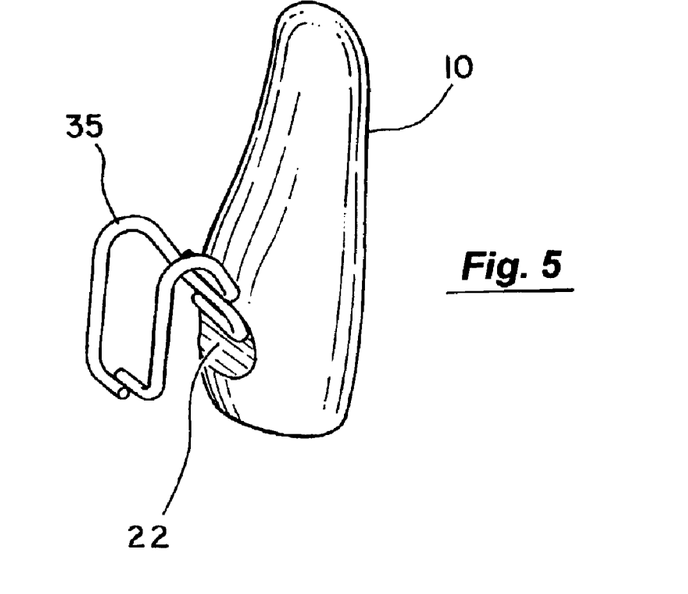
FIG. 5 is a rear perspective view of a model tooth 10 showing placement of an alternative embodiment of a lingual spring 35 in the gingival ideal reference groove 22 of the model tooth 10.

FIGS. 4 and 5 disclose, respectively, a central ideal reference groove 20 and a gingival ideal reference groove 22. A lab technician may install all three grooves around the lingual surfaces of the anterior, buccal and posterior segments of the teeth of a stone model. Any one such stone tooth may then look like the tooth 10 shown in FIG. 6. Of the three ideal reference grooves 20, 21, and 22 installed in the stone tooth 10 of FIG. 6, at most, only one will actually be used in conjunction with a force-generating spring 35 of the appliance 30 under typical conditions. The other two unused grooves should be understood as being inadvertent carry-through grooves that may be the result of grinding grooves appropriate to the corrective needs of adjacent teeth. Since the grooves ground by the lab technician are most accurately envisioned and formed by a continuous sweep of all of the teeth with the hand-held edge-cutting wheel, multiple grooves in the teeth may be common, and such multiple carry-through grooves may aid lab technician visualization Such multiple grooves nonetheless pose a problem at a later stage of the appliance fabrication process. Since the viscosity of the uncured acrylic mass that is cast within the confines of a stone model can be intentionally thickened around certain teeth, it is possible that the acrylic can significantly encroach on the crown of a tooth. Grooves in the stone teeth, particularly GIRG's provide opportunities for uncured acrylic to undesirably flow into such grooves. Once cured, the acrylic mass would have positive features formed by the negative concavity of such grooves. To avoid this, the laboratory technician can "wax in" the grooves, which replaces the stone material ground away, which serves to prevent uncured acrylic from flowing into the groove. In practice, a laboratory technician would typically balance the advantages of excessive grooving which aids visualization of the ideal arcs with the practical requirement that the grooves must later be waxed in prior to the casting of the dental acrylic portions of an appliance. Again, the problem of undesirable flow of uncured acrylic into the grooves and the solution of later waxing those groove applies only to situations where it is desirable to extend the acrylic portion of an appliance up onto the crown portion of a tooth.

The choice of which of as many as three ideal reference grooves 20, 21, and 22 are employed for treatment is a decision made by the lab technician. The technician's decision will depend on the type of correction required by any one tooth, and the most physiologically efficient level (gingival, central or occlusal) to apply the corrective force, as well as the physical configuration of the force-generating spring 35 available to exert that type of force.

Figure 7:
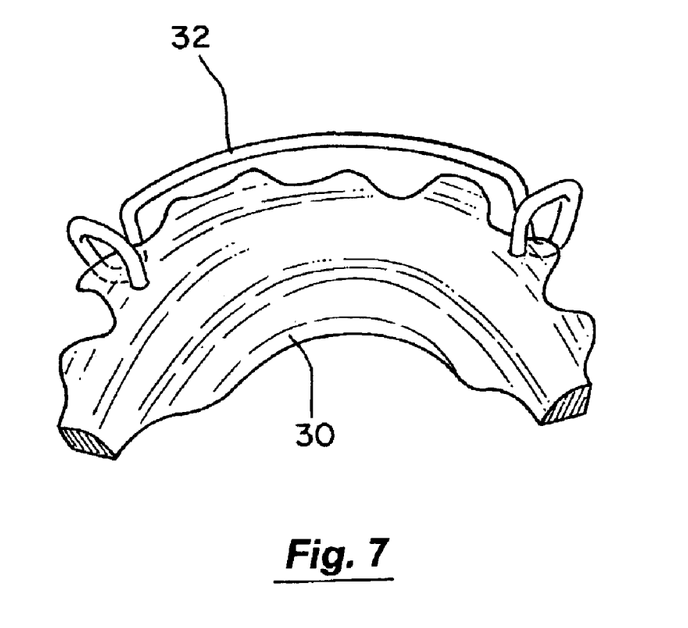
FIG. 7 is a rear perspective view of portion of an orthodontic appliance 30 with a labial bow 32.
Figure 8:
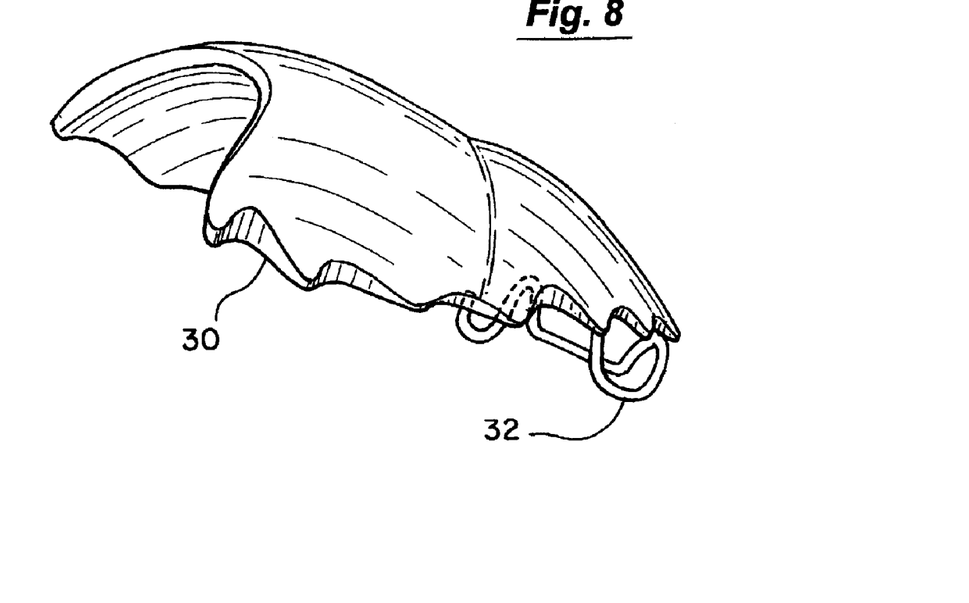
FIG. 8 is a side perspective view of an orthodontic appliance 30 with a labial bow 32 corresponding to FIG. 7.

Another active component of any lingual spring-based corrective force system-based appliance is the labial bow 32, which is almost universally present in acrylic-based orthodontic appliances 30. Two representative appliances with typical labial bow features are shown in FIGS. 7 and 8. The metallic labial bows 32 shown in FIGS. 7 and 8 span the labial surfaces of the teeth and act as a stop or barrier against further spring-driven labial movement of the anterior teeth. To appreciate the function of the labial bow 32, the corrective springs 35 positioned on the lingual side of the teeth push the teeth so as to move them so that they will eventually contact the labial bow 32. The outward pressure of the lingual springs 35 pushes the teeth against the labial bow 32 and once contact is made, any remaining need for rotational correction is played out by pushing the tooth against the rigidly fixed and ideally contoured labial bow 32. In this function, the labial bow 32 serves as a pattern or template against which the teeth are pushed into position.

Another function of the labial bow 32 should be considered. As a laboratory technician grinds the required ideal reference grooves 20–22 in the lingual surfaces of malpositioned stone teeth 10, some extremely mal-positioned teeth 10 may actually be cut in two. A severely lingually-positioned tooth for example may predict a groove so deep that the remaining stone material attaching the occlusal portion of the stone crown to the cingulum and lower part of the crown is structurally compromised or cut in two. In such cases, a laboratory technician will use base plate wax to adhere the stone tooth 10 securely to the labial bow 32 prior to installing such a groove in the model tooth. Wax material joining the stone tooth 10 to the labial bow 32 serves to hold all parts of the structurally compromised stone tooth 10 in true position even if cut in two.

During treatment with such an appliance, and once a tooth has been pushed toward and has made contact with the labial bow 32, the lingual spring 35 that has pushed the tooth into that position will have inherently spent its corrective force generation ability and will have become passive or so close to being passive that it is no longer capable of exerting a physiologically-effective tooth-moving force on a tooth. This is because the spring was originally positioned within the appliance 30 relative to the floor of the OIRG, CIRG or GIRG 20–-22, which as can be appreciated is coincident with the lingual side of the corrected tooth position at the end of the patient's orthodontic treatment. So it can be said then that three things occur roughly simultaneously: (1) Any one tooth can arrive at its desired, final treated position, just as; (2) The lingual spring pushing it into position "runs out of steam"; and (3) The tooth contacts the labial bow.

Since the labial bow 32 contacts any one tooth at a point near its central third, or stated differently, it contacts teeth at a point roughly equidistant between the incisal edge and the gingival margin, it can be seen that labially-directed forces from the lingual side of the tooth that are located in a gingival ideal reference groove 22 will tend to create an uprighting couple in a direction known as "negative torque." Negative torque sees the root of the tooth swing labially through the supporting bone. Conversely, labially-directed spring forces from the lingual side that are applied at an occlusal ideal reference groove 21 level will tend to upright a tooth in a positive torque direction.

So, as can be appreciated, the full corrective functioning of such appliances as described above involves the outward pressures of various configurations of lingual springs 35, applied at levels determined by the laboratory technician, inter-working with the stationary barrier of the labial bow 32. In this manner, teeth can be desirably repositioned in a labio-lingual direction, they can be uprighted as needed in torque, and they can be desirably rotated once up righted and moved against the labial bow. For the buccal and posterior segments, other standard rigidly-fixed structures well known in orthodontics, such as round arch wires, can serve as a barrier or stop, similar to the function of the labial bow 32 in the anterior portion of the arch. The various corrective dynamics described, as well as the ability of the group of lingual springs 35 described to effect rotational corrections completes a description of how such appliances 30 function in orthodontic treatment.

The present inventive methodology enables such appliances 30 to be constructed and fabricated in a way rendering them capable of applying very accurate and predetermined forces similar to the forces that are normally identifiable only through the time consuming and expensive process of anticipatorily resetting the patient's models. The present inventive methodology achieves the same high-quality results without resetting the teeth.

The above disclosure sets forth a number of embodiments of the present invention. Other arrangements or embodiments, not precisely set forth, could be practiced under the teachings of the present invention and as set forth in the following claims.

I claim:

1. A method for fabricating a removable orthodontic appliance having at least one lingual spring, said method comprising:
   creating a model of at least a portion of a patient's oral cavity and teeth;
   forming an ideal reference groove in the lingual surfaces of the model teeth reflecting the desired positions of the patient's teeth after orthodontic treatment; and
   casting an appliance on the model with at least one lingual spring having its stem embedded in the appliance and its tooth-contacting end in the reference groove of a model tooth.

2. The method of claim 1 wherein the ideal reference groove forms a substantially horizontal arc extending across a plurality of model teeth reflecting the desired arch form of the patient's teeth after orthodontic treatment.

3. The method of claim 1 wherein a plurality of ideal reference grooves are formed at different elevations on the lingual surface of the model teeth, and wherein the tooth-contacting end of each lingual spring is placed in one of the ideal reference grooves.

4. The method of claim 3 further comprising the steps of:
   selecting an ideal reference groove to be used for each tooth; and selecting an appropriate lingual spring for each tooth and its corresponding selected ideal reference groove from a plurality of available lingual springs having a range of sizes, shapes and physical properties.

5. The method of claim 1 wherein the ideal reference groove is formed in the central portion of the lingual surface of the model tooth.

6. The method of claim 1 wherein the ideal reference groove is formed in the gingival portion of the lingual surface of the model tooth.

7. The method of claim 1 wherein the ideal reference groove is formed in the occlusal portion of the lingual surface of the model tooth.

8. The method of claim 1 wherein casting of the appliance further comprises embedding the ends of a labial bow in the appliance.

9. A method for fabricating a removable orthodontic appliance having a plurality of lingual springs, said method comprising:

creating a model of at least a portion of a patient's oral cavity and teeth;

forming an ideal reference groove in the lingual surfaces of the model teeth as a substantially continuous horizontal arc extending across a plurality of model teeth to reflect the desired positions of the patient's teeth after orthodontic treatment; and casting an appliance on the model with a plurality of lingual springs, each lingual spring having its stem embedded in the appliance and its tooth-contacting end in the reference groove of a model tooth.

10. The method of claim 9 wherein a plurality of ideal reference grooves are formed at different elevations on the lingual surface of the model teeth, and wherein the tooth-contacting end of each lingual spring is placed in one of the ideal reference grooves.

11. The method of claim 10 further comprising the steps of:

selecting an ideal reference groove to be used for each tooth; and selecting an appropriate lingual spring for each tooth and its corresponding selected ideal reference groove from a plurality of available lingual springs having a range of sizes, shapes and physical properties.

12. The method of claim 9 wherein the ideal reference groove is formed in the central portion of the lingual surface of the model tooth.

13. The method of claim 9 wherein the ideal reference groove is formed in the gingival portion of the lingual surface of the model tooth.

14. The method of claim 9 wherein the ideal reference groove is formed in the occlusal portion of the lingual surface of the model tooth.

15. The method of claim 9 wherein casting of the appliance further comprises embedding the ends of a labial bow in the appliance.

* * * * *